United States Patent [19]
VomLehn et al.

[11] Patent Number: 5,978,696
[45] Date of Patent: Nov. 2, 1999

[54] REAL-TIME IMAGE-GUIDED PLACEMENT OF ANCHOR DEVICES

[75] Inventors: John Christian VomLehn, Scotia; Allen Lawrence Carl, Slingerlands; Harpal Singh Khanuja, Albany, all of N.Y.

[73] Assignee: General Electric Company, Schenectady, N.Y.

[21] Appl. No.: 08/944,277

[22] Filed: Oct. 6, 1997

[51] Int. Cl.$^6$ .................................................. A61B 5/00
[52] U.S. Cl. ..................... 600/411; 600/416; 600/417; 600/427; 600/429; 606/130
[58] Field of Search .................... 600/417, 411, 600/416, 427, 429, 414, 426; 345/418, 156; 606/130

[56] References Cited

U.S. PATENT DOCUMENTS

| | | | |
|---|---|---|---|
| 5,187,658 | 2/1993 | Cline et al. | |
| 5,271,400 | 12/1993 | Dumoulin et al. | 600/410 |
| 5,307,808 | 5/1994 | Dumoulin et al. | 600/423 |
| 5,318,025 | 6/1994 | Dumoulin et al. | 600/417 |
| 5,383,454 | 1/1995 | Bucholz | 600/429 |
| 5,443,066 | 8/1995 | Dumoulin et al. | 600/424 |
| 5,445,150 | 8/1995 | Dumoulin et al. | 600/424 |
| 5,776,064 | 7/1998 | Kalfas et al. | 600/429 |

*Primary Examiner*—Ruth S. Smith
*Attorney, Agent, or Firm*—Marvin Snyder; Douglas E. Stoner

[57] ABSTRACT

A real-time positioning system monitors and displays a real-time position and orientation (pose) of a surgical device relative to reference device and internal structures of a subject during a medical procedure. Tracking targets are affixed to a surgical device and a reference device. The reference device is fixed to a target site of a subject. The tracked targets are interactively monitored by a tracking device and their raw positions are converted to a position and orientation (pose) of the surgical device and the reference device. A medical imaging device acquires images of internal structures of the subject which is converted into computer models by a modeling engine. The models of internal structures are correctly registered with models of the surgical instrument and the reference device into a single interactive representation assisting a surgeon in a medical procedure. A density integrator may be employed to select a best path through a subject based upon user-defined criteria, such as greatest overall density, least density, furthest from nerves, blood vessels, intersecting the most diseased tissue, etc.

14 Claims, 1 Drawing Sheet

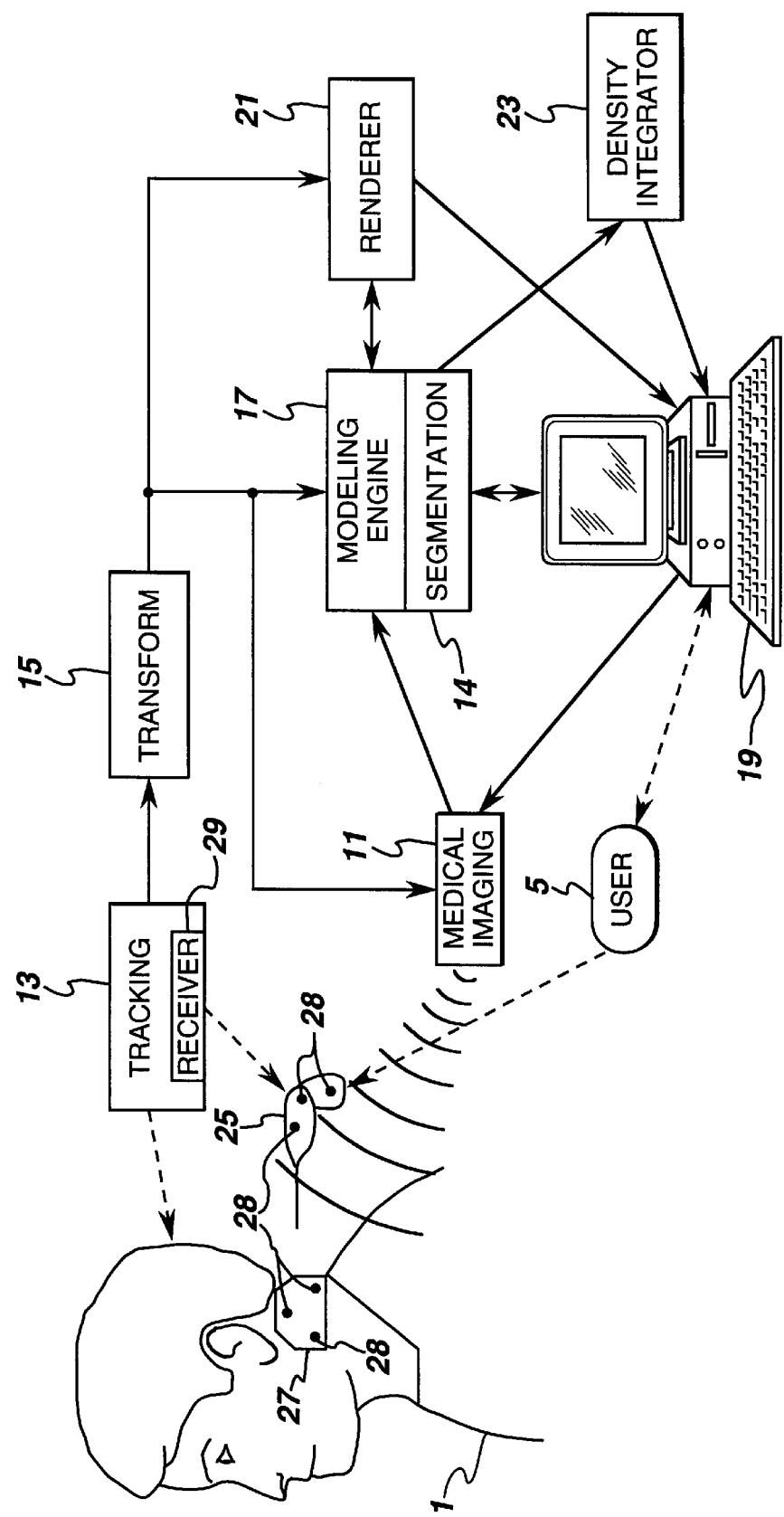

REAL-TIME IMAGE-GUIDED PLACEMENT OF ANCHOR DEVICES

1. FIELD OF THE INVENTION

The present invention relates to medical procedures in which a device is inserted into specified locations within a subject.

2. DESCRIPTION OF RELATED ART

In various medical procedures, it is necessary to attach a piece of medical equipment into a solid structure of the subject.

Typically, screws are inserted into vertebra on both ends of a structurally-compromised vertebrae to provide support while a spinal fusion is being created. Fractures in the spine and in other bones are also held together with a screw or similar implant.

In the case of abnormal spinal structure, it may necessary to fasten a support structure to correct or straighten a subject's spine.

These examples require precise insertion of a screw or pin into bone of the subject.

Typically, these pins or screws have been inserted by a surgeon who visually, or by 'feel', finds the approximate location where the screw or pin should be entered, and drills a hole at that location. The screw or pin is inserted into the hole.

Sometimes, during surgery, two dimensional (2D) snapshots such as x-rays or magnetic resonance (MR) images may be obtained.

Since these are 2D in nature, it may be difficult to extrapolate the image plane to the plane allowing the access of insertion of the screw.

Since the surgeon would also like to make as small an incision as possible, many times the target area is obscured by muscle or other tissue and the surgeon approximates the location of the actual target point.

Location of the target location may be further obscured by blood profusion in the area, further complicating identification of the target point.

Once the approximate location is determined, the surgeon has little information as to the relative strength and thickness of the bone in the area in which the pin or screw is to be inserted.

Also, while applying these screws and pins, it is possible that the surgeon punctures or severs major arteries, veins, or nerves which may be hidden inside tissue over the target structure, or lie behind the target structure, not visible to the surgeon.

Currently there is a need for a device which accurately indicates an optimum insertion point, orientation angle, and depth for surgical screws and pins.

SUMMARY OF THE INVENTION

A real-time positioning system aids a medical practitioner in accurately manipulating a surgical instrument to a precise position and orientation (pose) with respect to internal structures of a subject during a medical procedure.

The interactive positioning system employs tracked targets fixed to known locations of the surgical instrument and a reference device.

The reference device is attached to a desired target site on the subject.

A tracking device interactively tracks the raw location of the targets.

The raw location of the targets are converted into a pose of the surgical instrument and the reference device by a transform device coupled to the tracking device.

A medical imaging device is coupled to the transform device for receiving the pose of the surgical instrument and the reference device, and for acquiring volumetric imaging data internal structures of said subject near the location of the reference device.

A segmentation device coupled to the medical imaging device, receives the volumetric imaging data. It then identifies each segmented structure. A segmented structure is the set of contiguous locations in the imaging data having the data values within a predefined, or user-supplied range. The segmentation device creates models of the segmented structures selected by the user from the volumetric imaging data.

A modeling engine provides computer models of the reference and surgical devices. These may be predefined and stored.

A renderer device is coupled to the transform device and receiving the pose of the surgical device, and the reference device. It then interactively adjusts the pose of the computer models of the surgical and the reference devices for correct registration with models of the internal structures. It creates a display signal which is displayed to the user by a user interface. The user may also interact with the user interface to show or hide different internal structures. The user may also use the user interface to provide imaging, viewpoint or other user-supplied parameters into the system.

A density integrator may be employed which is coupled to a user interface. This allows the user to select a proposed region to use the surgical device. The user may also interact with density integrator to select a best pose for the medical instrument, and provide a visual representation superimposed upon the image of the surgical and reference devices and the internal segmented structures of the subject.

The user interacts with a user interface to select criteria for the best path. The criteria may require a path to be furthest from blood vessels, diseased tissue, hematoma, areas of reduced circulation, etc.

The user-defined criteria may also be finding a path with the greatest (or least) overall tissue density. Possible paths within a user-defined localized region are searched with an integration along each of the paths compared to find the highest (or lowest) density as the best path. This feature may become important for medical procedures, such as inserting fasteners at a pose which results in the greatest holding force.

OBJECTS OF THE INVENTION

It is an object of the present invention is to provide a device which interactively tracks the position and orientation of a reference device and an axis and tip of a surgery device and provides a visual representation of the relative locations and orientations of the reference device, surgical device and important structures of the subject.

Another object of the present invention is to provide a visual guide of a tip and access of the surgical device relative to a reference device attached to a living subject.

Another object of the present invention is to provide real-time image-guided placement of surgical screws or pins in a living subject.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

FIG. 1 is a simplified block diagram of one embodiment of the present invention in operation tracking the location of a surgical device relative to a desired location within a subject.

DETAILED DESCRIPTION OF THE INVENTION

The present invention operates by providing a computer graphic image indicating the position and orientation (pose) of a therapy device relative to a reference device fixed with respect to a subject 1. The therapy device, and reference device are correctly registered with images of internal images of subject 1. One type of therapy device is a surgical drill, which a user 5, preferably a surgeon manipulates.

A tracking device 13 tracks tracking targets 28 located on a therapy device 25 and a reference device 27. In one embodiment of the present invention, a Science Accessories model GP-12XL digitizer was used. This type uses sound transmitters as tracking targets 28. Tracking device 13 employs a receiver 29 and other electronics capable of calculating the instantaneous distance between each of the tracked targets 28.

At least three tracked targets 28 are required on each of therapy device 25 and reference device 27 in order to uniquely determine their pose.

A medical imaging device 11 acquires images of subject 1 and reference device 27 in the form of volumetric data which is passed to a modeling engine 17.

Medical imaging device 11 may be a computed tomography (CT), magnetic resonance (MR), ultrasound, or positron emission tomography (PET) imaging device. Other types of medical imaging device may also be used which provide an image of internal organs of subject 1 and can provide an image of tracked targets 28.

Medical imaging device 11 is connected to a transform device 15 which takes the coordinates from tracking device 13 and provides absolute pose of the reference device 27 and surgical device 25 from the raw locations of each of the tracked targets 28. The absolute locations of the reference device 27 may be used then by the medical imaging device 11 to obtain an image with the reference device 27 in the field-of-view and at a desired image plane angle.

Tracking device 13 is explained here using sound and time-of-flight technology to locate the therapy device 25 and reference device 27, however, other tracking means employing radio frequency (RF) tracking, MR tracking, or laser light interferometry tracking which are commonly used and known may be employed. Please note that a laser imaging and tracking device may be used only if there is a a clear line-of-sight between tracked targets 28 and tracking device 13.

An optical tracking device which may be used is that which is manufactured by Ascension Technology Corporation and Leica Corporation.

RF tracking is described in U.S. Pat. No. 5,443,066, Aug. 22, 1995 by Dumoulin, Darrow; U.S. Pat. No. 5,445,150, Aug. 29, 1995 by Dumoulin and Darrow.

MR tracking is described in U.S. Pat. No. 5,307,808, May 3, 1994 by Dumoulin, Darrow; U.S. Pat. No. 5,271,400, Dec. 21, 1993 by Dumoulin, Souza, Darrow; and U.S. Pat. No. 5,318,025, Jun. 7, 1994 by Dumoulin, Darrow.

All the above patents are assigned to the present assignee and are hereby incorporated by reference.

Therefore, various types of tracking devices 13 may be used with their associated tracked targets. In the case of MR tracking the target may be an MR active source, or an RF transmitter coil.

For RF tracking the tracked target may be an RF coil which either transmits or receives RF energy.

For laser distance measurement, the tracked target may be a laser reflective target, such as a corner cube reflector.

The present invention may be constructed in several different embodiments depending upon the speed and smoothness of imaging required and the complexity and power required of processing elements of the system.

In a basic embodiment, icons representing the therapy device 25 and reference device 27 are pre-stored in modeling engine 17 and are displayed on a user interface 19 in their proper pose. For example, if therapy device 25 is a surgical drill, a representation of the location of the tip of the drill and an axis from the tip of the drill through the drill bit uniquely defined the pose of the drill.

A reference device 27 which may be a triangular flat object, may be illustrated as a triangular flat plane having the proper pose.

In a more sophisticated embodiment, therapy device 25 and reference device 27 may be defined as a three dimensional surface model and provided to modeling engine 17, or be pre-stored in modeling engine 17. This allows modeling engine 17 to provide a view from a given viewpoint of either of these devices. This, of course, requires more processing power and more time.

A segmentation device 14 interacts with the volumetric imaging data from medical imaging device 11, and determines data values within a predefined range, or a range interactively defined by user 5 via interface 19. These values are used to define a tissue type. Next contiguous locations having the same tissue type are determined. The set of all contiguous locations of the same tissue type are treated as a solid structure. This information is passed to renderer 21.

Conventional segmentation may be used, such as that described in U.S. Pat. No. 5,187,658, Feb. 16, 1993 by Cline, and Lorensen, assigned to the present assignee and hereby incorporated by reference.

User 5 may interact with user interface 19 to specify imaging parameters to modeling engine 17 and a renderer 21, such as the viewpoints from which to view the model.

User 5 may interact with renderer 21 through user interface 19 to select different modes, such as one that user 5 is allowed to hide selected segmented structures, effectively 'stripping away' layers of tissue revealing deeper surfaces of internal structures. Conversely user 5 may show more superficial structures until the most superficial surface is shown.

The segmented models may then be provided to a renderer 21.

The images and models of subject 1 have to be coordinated with the models of therapy device 25 and reference device 27. Tracking device 13 tracks the locations of targets 28 and provides an absolute location with respect to the tracking device coordinate system. Medical imaging device 11 images targets 28 and provides relative locations, relative to the imaging scanner coordinate system. The relative locations are offset by renderer 21 to correspond to the locations of targets 28 from tracking device 13. This causes all models to become registered.

Other automated techniques such as a least squared error minimization of at least three points common to both of the systems may be used to register the locations measured by tracking device 13 to those of the medical imaging device 11.

The locations measured by tracking device 13 are combined with known information of the geometry of therapy device 25 and reference device 27 pre-stored in transform device 15 to determine the absolute pose of reference device 27 and therapy device 25. This information is provided to renderer 21 to rotate and translate reference device 27, therapy device 25 and the segmented images of subject 1 to their proper locations and orientations relative to each other. An image is provided to user 5 through user interface 19.

User 5 interacts with a user interface 19 to select criteria for the best path. The criteria may require a path to be furthest from blood vessels, diseased tissue, hematoma, areas of reduced circulation, etc. User 5 may then indicate on a screen of user interface 19 with a pointing device, such as a mouse, a region in which operator 5 wishes to examine along with an intended orientation. This may be in the form of a ray through the segmented structure. This region is searched to determine a ray which most closely fits the specified criteria, such as having the greatest cumulative distance from a vessel.

The user-defined criteria may also require finding a path with the greatest (or least) overall tissue density. A density integrator 23 is coupled to modeling engine 17 and receives the volumetric imaging data for a segmented structure selected by user 5. User 5 selects a local region to test. Density integrator 23 then searches pose of a plurality of rays integrating tissue density along each of the rays in the defined region identifying a ray which has highest density integral along the portion of a ray which an attachment device will traverse. If several exist, the closest to the orientation may be provided first.

One method which density integrator 23 determines the most solid tissue is by going back to the volumetric data for the selected segmented structure and integrating the data intersected by each ray. For CT scans this is very straightforward since the data is inversely proportional to tissue density.

In other types of medical imaging data, the data must first be adjusted to indicate tissue density. The imaging parameters may also be altered in order to acquire volumetric data indicating tissue density, and the procedure repeated with the new data. Not all medical imaging modalities may be suitable for optional density integrator 23 to operate.

Once the present invention is in operation, real-time tracking of internal structures of subject 1, reference device 27 and therapy device 25 are imaged on user interface 19 visible to user 5. User 5 may then interactively position the therapy device 25 to make it coincide with a proper pose indicated visually on user interface 19. This location has been pre-stored or has been previously calculated by density integrator 23.

In an embodiment employing a surgical drill, the present invention not only monitors the precise location to drill and the orientation, but may also indicate the proper depth. This indicate may be superimposed on the images, or alternatively an alarm or monitoring system may be activated indicating that the proper depth has been reached.

While several presently preferred embodiments of the novel invention been described in detail herein, many modifications and variations will now become apparent to those skilled in the art. It is, therefore, to be understood that the appended claims are intended to cover all such modifications and variations as fall within the true spirit of the invention.

What is claimed is:

1. A real-time positioning system for accurately positioning and orienting a surgical instrument, at a precise position and orientation (pose) with respect to internal structures and a target site of a subject during a medical procedure, comprising:
   a) a reference device fixed with respect to the target site of said subject;
   b) tracked targets fixed to known locations of the surgical instrument and the reference device;
   c) a tracking device for interactively tracking the raw location of the tracked targets;
   d) a transform device coupled to the tracking device for converting the raw locations of the tracked targets into a pose of the surgical instrument and the reference device;
   e) a medical imaging device coupled to the transform device for receiving the pose of the surgical instrument and the reference device, and for acquiring volumetric imaging data of said target site, reference device, tracked targets, and internal structures of said subject;
   f) a modeling engine for providing computer models of the reference device and surgical instrument;
   g) a segmentation device coupled to medical imaging device for creating computer models of contiguous locations in the volumetric imaging data having the data values within a predetermined, or user-defined, range indicating the same tissue type, being a segmented structure and for identifying surfaces between tissue type;
   h) a density integrator coupled to the modeling engine, the segmentation device and the user interface device, for receiving the volumetric data from the segmentation device for each user-defined segmented structure, and a user-defined region to search, and searching the user-defined region for a ray which best matches user-defined criteria;
   i) a renderer coupled to the segmentation device, the modeling engine, and the transform device for receiving the pose of the surgical device and the reference device, and for interactively creating a display signal of computer models of the reference and surgical devices in their appropriate pose in correct registration with models of the internal structures.

2. The real-time positioning system recited in claim 1, further comprising:
   a user interface coupled to the segmentation device, the modeling engine, the medical imaging device and the renderer for providing user-defined parameters to these devices; and for displaying the display signal from the renderer to the user.

3. The real-time positioning system recited in claim 1, wherein:
   a) the tracked targets comprise sonic energy emitters; and
   b) the tracking device comprises a sonic tracking device capable of tracking the locations of sonic energy emitters.

4. The real-time positioning system recited in claim 1, wherein:
   a) the tracked targets comprise radiofrequency (RF) energy emitters; and
   b) the tracking device comprises an RF tracking device capable of tracking the locations of RF energy emitters.

5. The real-time positioning system recited in claim 1, wherein:

a) the tracked targets comprise magnetic resonance (MR) coils; and b) the tracking device comprises an MR imaging device capable of tracking the locations of the MR coils.

6. The real-time positioning system recited in claim 1, wherein:

a) the tracked targets comprise light reflectors; and b) the tracking device comprises a light source capable of tracking the locations of light reflectors.

7. The real-time positioning system recited in claim 1, wherein the density integrator displays the ray found in said user defined region.

8. A real-time positioning system for accurately positioning and orienting a surgical instrument, at a precise position and orientation (pose) with respect to internal structures and a target site of a subject during a medical procedure, comprising:

a) a reference device fixed with respect to the target site of said subject;

b) tracked targets fixed to known locations of said surgical instrument and the reference device;

c) a tracking device for interactively tracking the raw location of the tracked targets;

d) a transform device coupled to the tracking device for converting the raw locations of the tracked targets into a pose of the surgical instrument and the reference device;

e) a medical imaging device coupled to the transform device for receiving the pose of the surgical instrument and the reference device, and for acquiring volumetric imaging data of said target site, reference device, tracked targets, and internal structures of said subject;

f) a modeling engine for providing computer models of the reference device and surgical instrument;

g) a segmentation device coupled to medical imaging device for creating computer models of contiguous locations in the volumetric imaging data having the data values within a predetermined, or user-defined, range indicating the same tissue type, being a segmented structure and for identifying surfaces between tissue type;

h) a density integrator coupled to the modeling engine, the segmentation device and the user interface device, for receiving the volumetric data from the segmentation device for each user-defined segmented structure, and a user-defined region to search, and for integrating the volumetric data indicating total tissue density, for each of a plurality of rays identifying maxima or minima in the region; and i) a renderer coupled to the segmentation device, the modeling engine, and the transform device for receiving the pose of the surgical device and the reference device, and for interactively creating a display signal of these computer models in their appropriate pose in correct registration with models of the internal structures.

9. The real-time positioning system recited in claim 8, further comprising:

a user interface coupled to the segmentation device, the modeling engine, the medical imaging device and the renderer for providing user-defined parameters to these devices; and for displaying the display signal from the renderer to the user.

10. The real-time positioning system recited in claim 8, wherein:

a) the tracked targets comprise sonic energy emitters; and b) the tracking device comprises a sonic tracking device capable of tracking the locations of sonic energy emitters.

11. The real-time positioning system recited in claim 8, wherein;

a) the tracked targets comprise radio frequency (RF) energy emitters; and b) the tracking device comprises an RF tracking device capable of tracking the locations of RF energy emitters.

12. The real-time positioning system recited in claim 8, wherein:

a) the tracked targets comprise magnetic resonance (MR) coils; and b) the tracking device comprises an MR imaging device capable of tracking the locations of the MR coils.

13. The real-time positioning system recited in claim 8, wherein:

a) the tracked targets comprise light reflectors; and the tracking device comprises a light source capable of tracking the locations of light reflectors.

14. The real-time positioning system recited in claim 8, wherein the density integrator displays a selected one of the plurality of rays found in said user defined region.

* * * * *